United States Patent [19]

Eriksson et al.

[11] 4,254,790

[45] Mar. 10, 1981

[54] PRESSURE CONTROL UNIT FOR THE CONTROL OF THE PRESSURE OF AT LEAST ONE GAS DEPENDING ON THE PRESSURE OF ANOTHER GAS

[75] Inventors: Einer Eriksson; Johannes Jensen, both of Odense M.; Jørgen S. Lundsgaard, Troense, all of Fed. Rep. of Germany

[73] Assignee: Innoventa ApS, Denmark

[21] Appl. No.: 937,942

[22] Filed: Aug. 30, 1978

[30] Foreign Application Priority Data

Aug. 30, 1977 [DK] Denmark .............................. 3849/77

[51] Int. Cl.³ ............................................. G05D 11/03
[52] U.S. Cl. ..................................................... 137/100
[58] Field of Search ................................... 137/98, 100

[56] References Cited

U.S. PATENT DOCUMENTS

| | | | |
|---|---|---|---|
| 1,035,576 | 8/1912 | Goodwin et al. | 137/98 |
| 1,573,079 | 2/1926 | McKee | 137/98 |
| 3,324,872 | 6/1967 | Cloud | 137/98 |

FOREIGN PATENT DOCUMENTS

| | | | |
|---|---|---|---|
| 7003356 | 3/1969 | Netherlands | 137/98 |
| 1023900 | 3/1953 | France | 137/98 |

*Primary Examiner*—William R. Cline
*Assistant Examiner*—H. Jay Spiegel

[57] ABSTRACT

A pressure control unit comprises a central reference chamber in which the gas pressure is adjustable and one or more control chambers, each of which is separated from the reference chamber by a membrane system which consists of two interconnected membranes having a predetermined ratio of their surface areas. Each membrane system is connected to a valve for controlling the flow of a gas to the respective control chamber whereby the pressure therein varies in proportion to the reference pressure.

3 Claims, 1 Drawing Figure

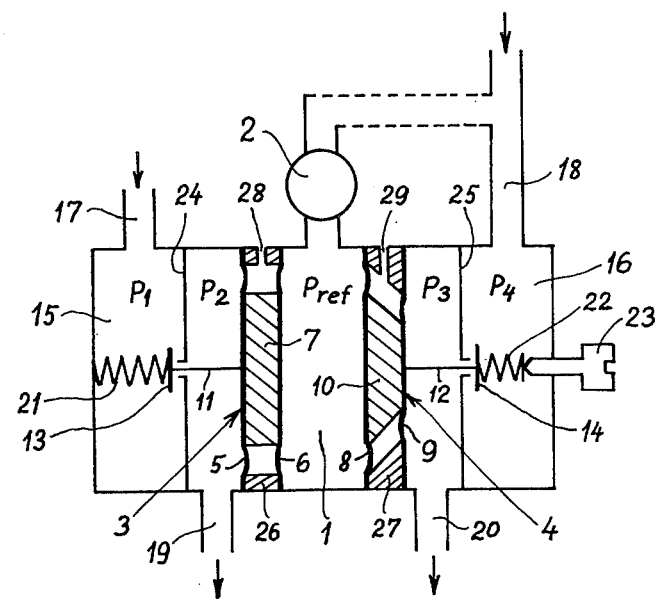

PRESSURE CONTROL UNIT FOR THE CONTROL OF THE PRESSURE OF AT LEAST ONE GAS DEPENDING ON THE PRESSURE OF ANOTHER GAS

BACKGROUND OF THE INVENTION

The present invention relates to a pressure control unit for the control of at least one gas depending on the pressure of another gas comprising a reference pressure chamber, in which the pressure is adjustable, and at least one control chamber, through which the gas to be controlled is lead, control chamber being separated from the reference chamber by means of a membrane system, which is connected to a spring-loaded control valve in the gas inlet to the control chamber.

A pressure control unit of this kind is known in which one gas is supplied to the reference pressure chamber via a usual pressure regulator and the pressure in the reference pressure chamber causes a corresponding control of the pressure of the other gas which is supplied to the control chamber. By changing the pressure in the reference chamber an equal change of the pressure of the other gas is provided as a constant pressure difference is maintained between the two gases determined mainly by the elastic forces of the membrane system and the spring-load of the control valve.

This control with a constant pressure difference results in a varying ratio of the pressures when these are changed, which, however, is adverse to most applications and it has therefore often been attempted to overcome this drawback by different measures.

The object of the present invention is to provide a proportional pressure control of one or more gases depending on the pressure of another gas, i.e. a simultaneous control of the pressures, so that the ratio of them remains essentially constant when they are changed.

SUMMARY OF THE INVENTION

According to the invention such control is obtained by the fact that the membrane system or at least one of the membrane systems consists of two mutually firmly connected membranes with a predetermined ratio of their surface areas, such that the force on one membrane is transmitted to the other membrane.

As long as the elastic forces of the springs of the control valves and of the membranes and the pressure difference across the valves are relatively small compared with the gas pressures, the invention results in the pressure in the control chamber or chambers being varied essentially in proportion to the reference pressure since the product of the membrane area and gas pressure on both sides of the membrane system may then be considered substantially equal. When two or more control chambers are provided, which chambers are each separated from the reference chamber by a membrane system, the result of controlling both or all gas pressures in the same way through control chambers by means of the same reference chamber and reference is that the influence on the pressures originating from the elastic forces of the control valve springs and membranes and the pressure difference across the valves are substantially equalized, so that the ratio of the outlet pressures in the control chambers within a range approximately depends only on the ratio of the membrane areas, as explained in more detail in the example below.

In order to obtain a better approximation of the pressure ratio to the ratio of the membrane areas when at least two control chambers are provided the surface area of the membrane systems facing the reference chamber can be of equal size according to the invention.

According to the invention a further approximation can be obtained when the spring-load of at least one of the control valves is adjustable. It will then be possible to balance the above mentioned elastic forces completely.

BRIEF DESCRIPTION OF THE DRAWING

The single FIGURE shows a view, partly schematically and partly in cross section, of an embodiment of a pressure control unit according to the invention for the simultaneous control of two gas pressures.

DESCRIPTION OF THE PREFERRED EMBODIMENT

The control unit shown in the drawing consists of a central reference chamber 1, in which the pressure is controlled by means of a usual pressure regulator 2 with an relief valve (not shown). The reference chamber has no outlet, pipe, so the relief valve is necessary to enable reduction of the pressure.

At either side of the reference chamber 1 a membrane system 3 and 4, respectively, has been mounted. Each membrane system consists of two membranes 5,6 and 8,9, respectively, of an elastic material, such as rubber, which are fastened to either side of a membrane body 7 and 10, respectively, of any suitable trary material, so that each membrane system moves as a unit.

The membrane systems are connected by means of connecting bars 11 and 12 to valves 13 and 14, respectively, in control chambers 15 and 16, located outside the membrane systems 3 and 4, respectively. The control chambers have gas inlet pipes 17 and 18 and outlet pipes 19 and 20. Each control valve 13 and 14 consists as shown of a valve body connected to the membrane system and being pressed against a valve seat by a spring 21 and 22, respectively. An adjustment screw 23 controls the load of the spring 22. If so desired the spring 21 can of course also be provided with an adjustment screw.

Each control chamber 15 and 16 is divided by means of a wall 24 and 25, respectively, into an inlet chamber and outlet chamber, which are connected to the inlet and outlet pipes, respectively. As shown the reference chamber is connected to the inlet pipe 18, but may also be connected to a separate pressure source.

The membrane systems 3 and 4 are inserted into the walls 26 and 27 which separate the control chambers 15 and 16 from the reference chamber, the individual membranes being fastened to these walls so that cavities are formed between the membranes around the membrane bodies 7 and 10, respectively, which are vented to the atmosphere through holes 28 and 29 in the said walls. The membranes 5,6 and 8 are of equal size in the embodiment shown, whereas membrane 9 is of a different size.

The pressure in the reference chamber 1 being designated $P_{ref}$, and the inlet pressure and outlet pressure in the control chamber 15 being designated $P_1$ and $P_2$, the following equation can be set up for the membrane system 3 and the control chamber 15

$$P_{ref} \cdot A = P_2 \cdot A + (P_1 - P_2) \cdot a + F_{sl} \qquad (1)$$

where A is the effective area of the two membranes 5 and 6 and a is the effective area of the valve body 13, while $F_{sl}$ constitutes the total elastic forces of the two membranes and the valve spring 21.

The inlet pressure and outlet pressure in the control chamber 16 being designated $P_3$ and $P_4$, respectively, an equation can be set up in a similar manner for the membrane system 4 and the control chamber 16

$$P_{ref} A = P_3 \cdot A_3 + (P_4 - P_3) \cdot a + F_{s2} \qquad (2)$$

where A is the area of the membrane 8, $A_3$ is the effective area of the membrane 9 and $F_{s2}$ is the total elastic forces of the membranes 8 and 9 and the valve spring 22.

When the inlet pressures $P_1$ and $P_4$ of the two gases are relatively small (e.g. less than $4 \times 10^5$ Pa) and the effective areas of the valve bodies are small the terms $(P_1 - P_2) \cdot a$ $(P_4 - P_3) \cdot a$ will be negligible. Small differences, if any, between the elastic forces $F_{sl}$ and $F_{s2}$ of the membranes and the valve springs can be neutralized by means of adjustment screws, such as the screw 23. Under these circumstances $$P_3 / P_2 = A / A_3 \qquad (3)$$

can be derived from equations (1) and (2).

Equation (3) indicates that the ratio of the outlet pressures of the two gases depends only on the ratio of the areas A and $A_3$ of the membranes 8 and 9. If the ratio of the outlet pressures has to be changed, it will only be necessary therefore to change the ratio of the areas of the membranes 8 and 9.

Although it has been assumed above that the membranes 5 and 6 are of equal size and have the same area as membrane 8, it is to be understood that they may also be of different sizes, in which case an approximately constant ratio of the outlet pressures of the two gases is still obtained. This ratio, of course, also depends on the ratio of the areas of the membranes in the membrane system 3. When the membranes in a membrane system are of equal size, as in the case of the membranes 5 and 6, these may, of course, also be replaced by a single membrane.

Although a control unit with two control chambers 15 and 16 has been described in the above, it is to be understood that further control chambers with associate membrane systems may be connected to the reference chamber 1. In such case the noted reference chamber is to be formed having a suitable polygonal form.

A control unit according to the invention has been used for supplying a digital gas mixer for anaesthesic purposes the two gases to be mixed being $O_2$ and $N_2O$. The ratio of the dynamic viscosities of these gases in 1:4 at room temperature, and the inlet pressures to the gas mixer must consequently have this ratio. According to equation (3) above this also determines the ratio of the areas of the membranes 8 and 9. The required flow of each gas is from $10^{-6}$ to $10^{-4}$ m$^3$/sec. In the embodiment applied the three membranes 5,6 and 8 had an area of $2.2 \times 10^{-3}$ m$^2$ and the membrane 9 had an area of $1.6 \times 10^{-3}$ m$^2$. These areas fit well with equation (3) in spite of the fact that the effective membrane area usually is smaller than the physical membrane area. Measurements have shown that it is possible to obtain a total accuracy of the partial pressures of the gases higher than 99% with the proportional pressure control unit described.

With the gases mentioned above oxygen is supplied to the control chamber 16 and reference chamber 1. Thereby the supply of $N_2O$ will stop if the oxygen pressure disappears. This is an important factor in the field of anaesthesiology, because a supply to the patient of $N_2O$ only might be fatal.

We claim:

1. A pressure control apparatus for the simultaneous control of the pressure of at least two gases, said apparatus comprising:
    means defining a reference pressure chamber to which a fluid at an adjustable pressure can be supplied,
    means defining at least two control chambers positioned adjacent said reference pressure chamber, each of said control chambers having a gas inlet, a gas outlet and a valve means located therebetween, and
    separate membrane systems positioned between each of said control chambers and said reference pressure chamber, each membrane system including a spring-loaded control valve extending into the adjacent control chamber so as to control gas flow through the respective valve means therein, and each membrane system comprising two spaced apart membranes which are mutually firmly interconnected, the surface areas of the respective membranes of each membrane system which face the reference pressure chamber being equal, whereas the surface areas of the respective membranes of each membrane system which face the respective control chambers differing, the membrane systems functioning such that the ratio of gas pressures emanating from the various control chambers will remain constant, said pressure ratio being determined by said differing surface areas of said respective membranes.

2. A pressure control apparatus as defined in claim 1 wherein means are provided to adjustably control the bias on at least one of said spring-loaded control valves.

3. A pressure control apparatus as defined in claim 1 wherein means are provided to simultaneously supply a single gas to both said reference pressure chamber and at least one of said control chambers.

* * * * *